United States Patent
Ewing et al.

(10) Patent No.: US 8,019,466 B2
(45) Date of Patent: Sep. 13, 2011

(54) DEVICES AND METHODS FOR DETECTING HAZARDOUS MATERIALS

(75) Inventors: Kenneth James Ewing, Crofton, MD (US); Fred Whiton, Jr., Towson, MD (US); Paul George Kahl, Jr., Perry Hall, MD (US); John Paul Santori, Ellicott City, MD (US)

(73) Assignee: Northrop Grumman Systems Corporation, Los Angeles, CA (US)

( * ) Notice: Subject to any disclaimer, the term of this patent is extended or adjusted under 35 U.S.C. 154(b) by 1118 days.

(21) Appl. No.: 11/812,076

(22) Filed: Jun. 14, 2007

(65) Prior Publication Data

US 2008/0312768 A1 Dec. 18, 2008

(51) Int. Cl.
*G06F 7/00* (2006.01)
(52) U.S. Cl. .................................... 700/225; 700/230
(58) Field of Classification Search .............. 700/225, 700/230; 702/27; 73/865.8; 356/301
See application file for complete search history.

(56) References Cited

U.S. PATENT DOCUMENTS

| | | | |
|---|---|---|---|
| 5,585,575 A * | 12/1996 | Corrigan et al. | 73/863.71 |
| 2003/0145664 A1* | 8/2003 | Schwarz et al. | 73/863.22 |
| 2005/0080520 A1* | 4/2005 | Kline et al. | 701/1 |
| 2005/0274788 A1* | 12/2005 | Craig | 235/375 |
| 2006/0203238 A1* | 9/2006 | Gardner et al. | 356/301 |
| 2008/0034901 A1* | 2/2008 | Beck | 73/865.8 |

* cited by examiner

*Primary Examiner* — Gene Crawford
*Assistant Examiner* — Ramya Prakasam
(74) *Attorney, Agent, or Firm* — Andrews Kurth LLP (57) ABSTRACT

A container screening system that uses multiple orthogonal sensors for detecting hazardous materials, such as liquid explosives and precursors of liquid explosives, in sealed containers. The container screening system comprises a first sensor that detects materials inside the container using a first detection technology, a second sensor that detects materials insider the container using a second detection technology, and a data processing unit that processes data from the first and second sensors and generates a screen result. The system reduces false positives and increases probability of detection by matching the relative strengths and weaknesses of each technology.

18 Claims, 7 Drawing Sheets

DEVICES AND METHODS FOR DETECTING HAZARDOUS MATERIALS

FIELD OF INVENTION

This invention relates generally to detection of hazardous materials and, in particular, to detection of hazardous materials, such as liquid explosives and precursors of liquid explosives, in sealed containers.

BACKGROUND

In light of the increasing threat of terrorism, improved explosive detection systems and methods are urgently needed for use at security checkpoints, such as those located at airports and other transportation hubs. While there are several liquid explosives, such as nitroglycerine and picatinny liquid explosive (PLX), that could be used to bring down an aircraft, these liquid explosives are generally too unstable or too easily detected to be readily smuggled aboard. Terrorists are more likely to use two or more liquids that are stable by themselves, but which form a powerful explosive when mixed together. A prime candidate for this approach would be triacetone triperoxide (TATP). The raw ingredients of TATP are liquids that could potentially be carried on board in sufficient quantities in containers such as bottles of shampoo or contact lens solution.

Because of the nature of liquid binary explosives, detection based on particles on the surface of a container is difficult if not impossible. In addition, effective screening of liquid explosives requires the ability to detect the explosives in sealed containers. Although a number of devices have been developed for such purpose, they typically use a single detection technology that often produces false positive readings.

Accordingly, there still exist a need for container screening systems and methods with low false positive rate and high probability of detection.

SUMMARY OF THE INVENTION

One aspect of the present invention relates to a container screening system for detecting hazardous materials in sealed containers. The container screening system comprises a Universal Product Code (UPC) reader that reads UPC barcode from the container, a first sensor that detects materials inside the container using a first detection technology, a second sensor that detects materials inside the container using a second detection technology, and a data processing unit that processes data from the first sensor and the second sensor and generates a screen result, wherein the UPC reader is used as a queuing device for the first and second sensor and wherein the second detection technology is different from the first detection technology.

In one embodiment, the first detection technology is ultrasonics and the second detection technology is Raman spectroscopy.

In one embodiment, the container screening system further comprises a third sensor that detects materials inside the container using a third detection technology that is different from the first detection technology and the second detection technology.

In another embodiment, the third detection technology is neutron activation analysis.

In another embodiment, the container screening system further comprises a conveyor system that transports containers.

In another embodiment, the container screening system further comprises a display device that displays the screen result.

In another embodiment, the container screening system further comprises a marking device that places a mark on said container after screen showing the container is safe.

In another embodiment, the data processing unit of the container screening system comprises a microprocessor and a memory that is used to store sensor signatures of hazardous and non-hazardous materials.

In yet another embodiment, the hazardous materials comprises liquid explosives and precursors of liquid explosives.

Another aspect of the present invention relates to a method of screening a container for hazardous materials. The method comprises the steps of first scanning the UPC on the container and generating UPC data to queue the system as to the likely contents of the container. Then the container is subjected to a first inspection with a first sensor using a first detection technology and generating first sensor data; subjecting the container to a second inspection with a second sensor using a second detection technology and generating second sensor data; and producing a screen result based the UPC data, the first sensor data and the second sensor data, wherein the first detection technology is different from the second detection technology.

In another embodiment, the method further comprises the step of subjecting the container to a third inspection with a third sensor using a third detection technology and generating a third sensor data, wherein the third detection technology is different from the first detection technology and the second detection technology, and wherein the screen result is produced based on the UPC data, the first sensor data, the second sensor data, and the third sensor data.

In another embodiment, the first detection technology is ultrasonics, the second detection technology is Raman spectroscopy, and the third detection technology is neutron activation analysis.

In another embodiment, the method further comprises the step of marking the container based on the screen result as safe.

In yet another embodiment, the method further comprises the step of displaying the screen result on a display device.

Yet another aspect of the present invention relates to a method of screening a container for hazardous materials. The method comprises the steps of scanning the container for UPC barcode with a UPC reader and generating UPC data which is used to queue the remaining detection technologies; subjecting the container to a first inspection with a first sensor using a first detection technology and generating first sensor data; subjecting the container to a second inspection with a second sensor using a second detection technology and generating second sensor data; determining the identities of materials inside the container based on the UPC data; the first sensor data, and the second sensor data; if all materials inside the container are identified as non-hazardous materials, allowing the container to pass inspection; if one or more materials inside the container is identified as hazardous materials, transporting the container to a storage device; if one or more materials inside the container cannot be identified by the first detection technology and the second detection technology, subjecting the container to a third inspection with a third sensor using a third detection technology and generating a third sensor data, and identifying the one or more materials that cannot be identified by the first detection technology and the second detection technology based on the third sensor data.

In one embodiment, the first detection technology is ultrasonics, the second detection technology is Raman spectroscopy, and the third detection technology is neutron activation analysis.

DETAILED DESCRIPTION OF THE INVENTION

In describing preferred embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose.

One aspect of the present invention relates to a container screening system for detection of hazardous materials in sealed containers. Because of the complex nature of liquid materials and the various containers that contain them, the detection system for hazardous materials must be able to discriminate between everyday liquids, such as water and sport drinks, and hazardous liquid materials, such as liquid explosives or precursors of liquid explosives. In order to achieve this level of detection, the detection system of the present invention utilizes multiple orthogonal detection technologies that are complementary to each other in detecting power, and an algorithm that fuses data from different sensors, thereby lowering the number of false positives and increasing the probability of detection.

Table 1 provides a list of possible detection technologies that can be used in the detection system of the present invention. This table compares the capabilities of stand alone technologies for detection of liquid explosives. The letter "Y" means the technology meets the requirement, the letter "P" means the technology partially meet the requirements, and the letter "N" means the technology does not meet the requirements. By matching the relative strengths and weaknesses of each technology in Table 1, a system of detector technologies exhibiting low false positives and high probability of detection can be designed.

TABLE 1

Possible detection technologies for liquid explosives

| Requirements | Technology | | | | | | | | |
|---|---|---|---|---|---|---|---|---|---|
| | Ultrasonic | Raman | Neutron Activation | NMR | NQR | Microwave | Terahertz | X-ray | X-ray (Fl) |
| Detect: | | | | | | | | | |
| explosive liquids | P | Y | P | P | Y | P | P | P | P |
| flammable liquids | P | Y | P | P | Y | P | P | P | P |
| Distinguish from: | | | | | | | | | |
| drinks | Y | Y | Y | Y | Y | Y | Y | P | P |
| lotions | P | Y | Y | Y | Y | Y | Y | P | P |
| hygiene products (gels,paste) | P | Y | Y | Y | Y | Y | Y | P | P |
| contact lens solutions | Y | Y | Y | Y | Y | Y | Y | P | P |
| Throughput | | | | | | | | | |
| 200 bottles per hour | Y | Y | Y | P | P | P | Y | Y | P |
| full or partially full | Y | Y | P | Y | Y | Y | Y | Y | |
| any shape | P | Y | Y | Y | Y | P | Y | Y | Y |
| any color | Y | N | Y | Y | Y | Y | Y | Y | Y |
| glass | Y | Y | Y | Y | Y | Y | Y | Y | Y |
| paper | Y | P | Y | Y | Y | Y | Y | Y | Y |
| plastic | Y | P | Y | Y | Y | Y | Y | Y | Y |
| metal | Y | N | Y | N | N | N | N | Y | Y |
| TRL5 or greater | Y | Y | Y | Y | Y | Y | Y | Y | Y |
| Comments | 1, 2 | 3 | 6 | 4, 5 | | 1, 2 | | 2 | 7 |

1 Need to measure size and temperature
2 Not know to be very sensitive
3 highly selective
4 expensive
5 low signal level
6 Requires larger quantities
7 Will not detect below Na on periodic table
Y meets requirements,
P partially meets requirements,
N does not meet requirements,
NMR nuclear magnetic resonance,
NQR nuclear quadrupole resonance.

Figure 1:
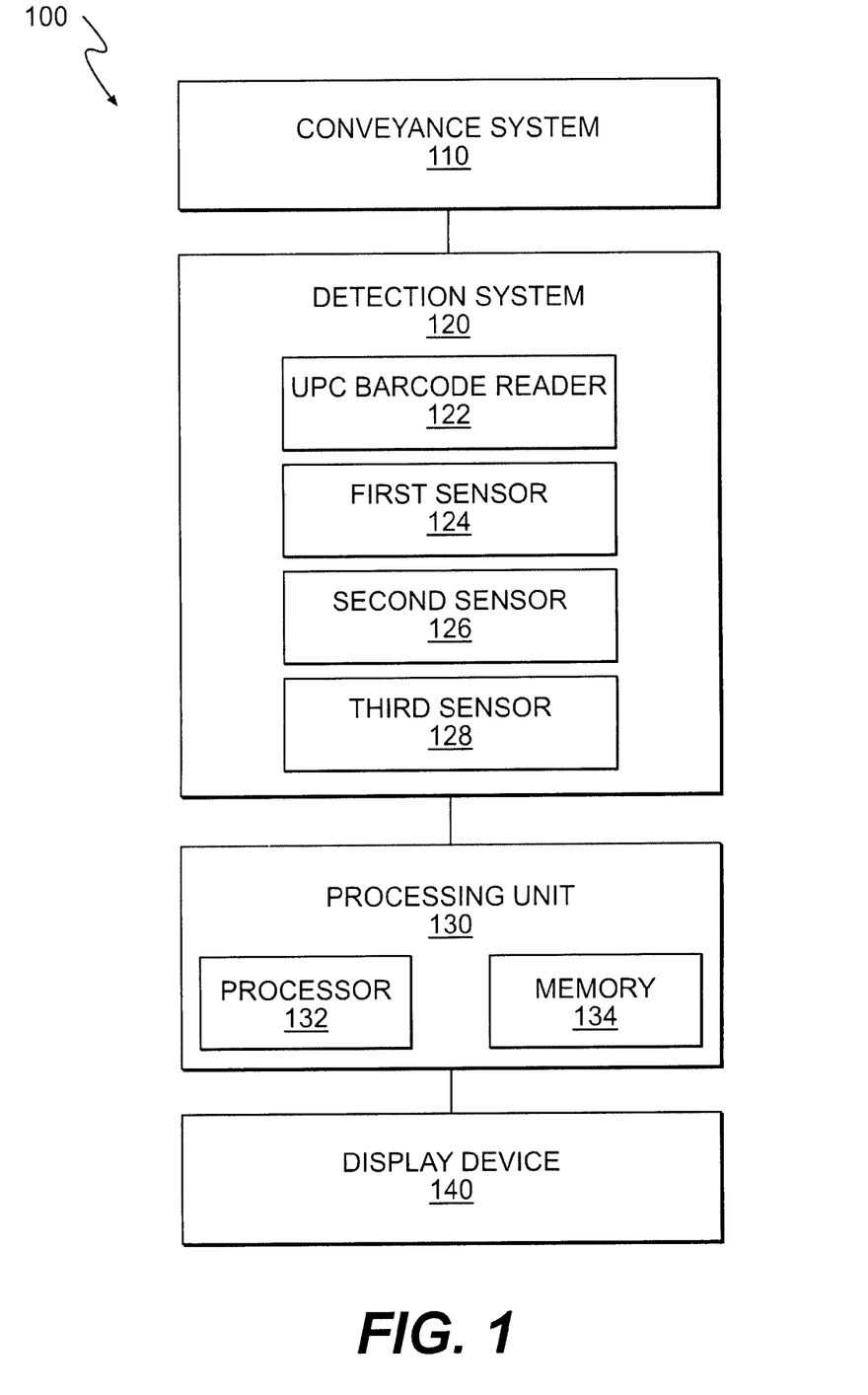
FIG. 1 is a diagram showing one embodiment of the container screening device of the present invention.

FIG. 1 is a diagram of an embodiment of the container screening system of the present invention. The container screening system 100 comprises a detection system 120 having a UPC reader 122 that acts to queue for the other detection technologies, and at least a first sensor 124 and a second sensor 126 that are capable of detecting liquid hazardous materials in a container using different detection technologies, and a processing unit 130 having a microprocessor 132 and a memory 134. The processing unit obtains sensor data from detection system 120, analyzes the data using an algorithm and a sensor signature library stored in the memory 134, and generates a screen result. As shown in FIG. 1, the container screening system 100 may further comprises a conveyance system 110 for transporting containers in need of inspection, and a display device 140 to display the screen results. The detection system 120 may further contain a third sensor 128 that uses a third detection technology.

As used herein, the term "container" refers to containers of any size and shape. The container can be made of glass, plastics, metal, paper or any other materials suitable for the purpose of containing a liquid.

The hazardous liquid materials include liquid explosives such as nitroglycerine, triacetone triperoxide (TATP), and PLX; precursors of liquid explosives such as nitric acid, sulfuric acid, methanol, formaldehyde, acetone, glycerol, and hydrogen peroxide, as well as other flammable, corrosive, and toxic hazardous liquid materials regulated by the Department of Transportation (Title 49 CFR Parts 100-185).

The first sensor 124 and second sensor 126 use different detection technologies that are complementary to each other in detection power. In one embodiment, the technologies are ultrasonic detection and Raman spectroscopy. The third sensor 128 uses yet another detection technology. In one embodiment, the third detection technology is neutron activation analysis. One skilled in the art would understand that the container screening system 100 may employ more than three detection technologies and many other combinations of detection technologies may be used.

Ultrasonic technology (ultrasonics) has been widely used in the medical field for soft tissue imaging and in industry for detection of defects in solid materials. To monitor the composition of a liquid in a container, a pulse of ultrasonic energy is applied to the liquid material in the container and an echo signal is detected from the opposite end of the container. The elapsed time between the applied pulse and the echo signal (i.e., the transit time) is measured and compared to those of various reference materials to determine the liquid's composition.

Raman spectroscopy is based upon the interaction between optical radiation and various chemical species present in a sample. When the sample is irradiated with optical radiation a fraction of the optical radiation is scattered by the molecules in the sample. The scattered radiation differs from the wavelength of the initial radiation by an amount proportional to the vibrational modes within the target molecules. The difference between the scattered radiation and incident beam, termed the Raman shift, corresponds to molecular vibrations in the target molecule. The degree of Raman shift is dependent upon the chemical structure of the molecules causing the scattering. During irradiation, the spectrum of the scattered radiation is measured with a spectrometer. In a preferred embodiment, the detection technology is fiber optic Raman spectroscopy.

Neutron activation represents a most recent advance in luggage scanning techniques. The technique depends upon bombardment of the testing material, such as the liquid in a container, with low-energy neutrons and then detect signature emissions from hazardous materials. For example, the neutrons cause nitrogen, which is a constituent of most explosives, to emit gamma radiation that can be detected and analyzed by computer Table 2 shows that an integrated system incorporating the three technologies, Raman, ultrasonics, and neutron activation analysis will meet all requirements for a container screening system. For example, ultrasonic signature matching or neutron activation analysis alone are marginal detecting and identifying explosive or flammable liquids. However, in combination with Raman spectroscopy which generates a fingerprint of the material, the system will be capable of detecting and identifying the presence of an explosive or flammable liquid. Table 2 also shows that Raman spectroscopy cannot detect substances contained in either metal or opaque plastic and glass, however, combining ultrasonics and neutron activation analysis allows for discrimination of hazardous substances from common substances in metal or opaque containers.

TABLE 2

Comparison of three technologies for liquid screening system

| | Technology | | |
|---|---|---|---|
| Requirements | Ultrasonic | Raman | Neutron Activation |
| Detect | | | |
| explosive liquids | P | Y | P |
| flammable liquids | P | Y | P |
| Distinguish from: | | | |
| drinks | Y | Y | Y |
| lotions | P | Y | Y |
| hygiene products (gels, paste) | P | Y | Y |
| contact lens solutions | Y | Y | Y |
| Throughput | | | |
| 200 bottles per hour | Y | Y | Y |
| full or partially full | Y | Y | P |
| any shape | | Y | Y |
| any color | Y | N | Y |
| glass | Y | Y | Y |
| paper | Y | P | Y |
| plastic | Y | P | Y |
| metal | Y | N | Y |

Y meets requirements,
P partially meets requirements,
N does not meet requirements.

Figure 2:
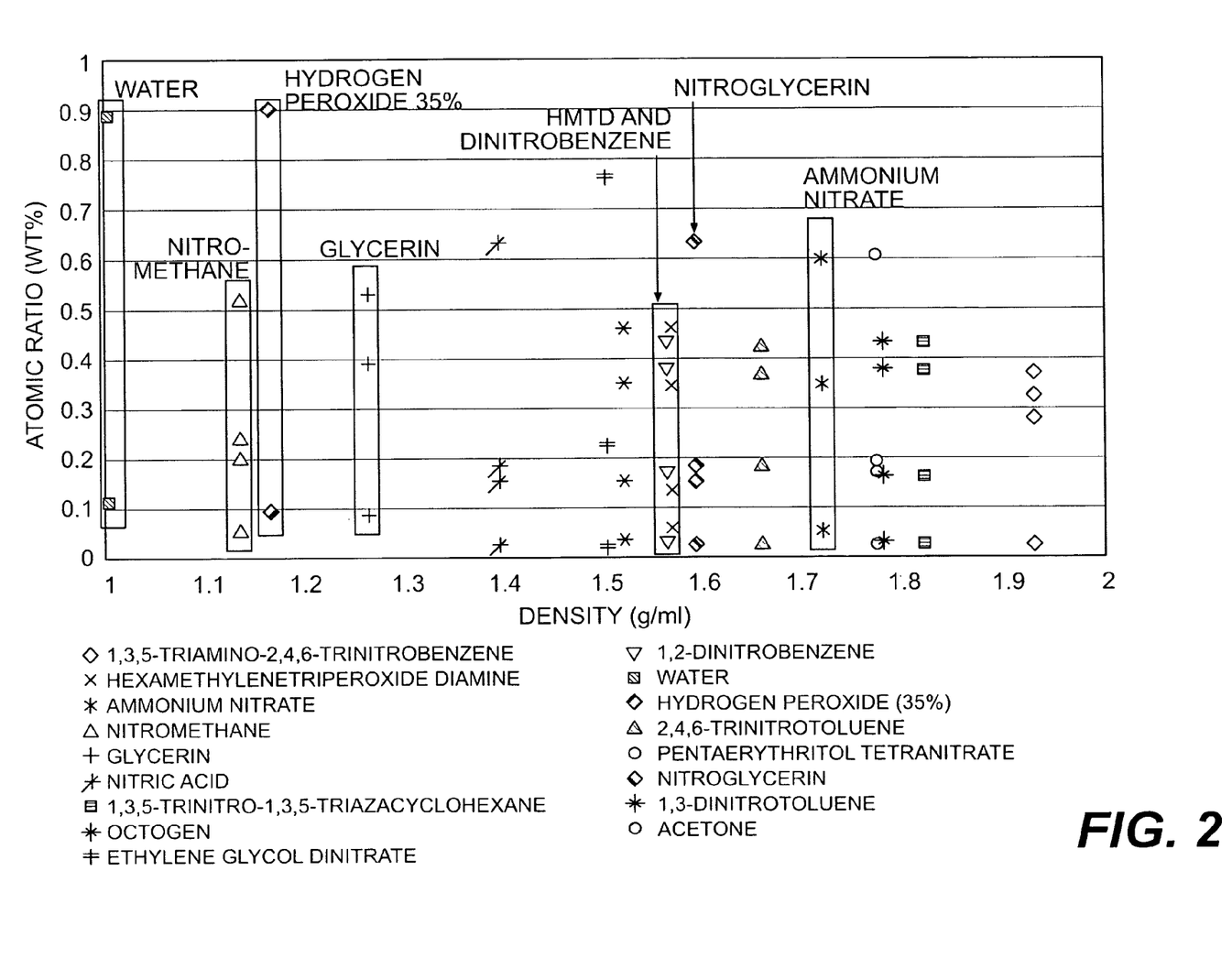
FIG. 2 is a diagram showing the discriminating power of a combined ultrasonic/neutron activation analysis sensor system.

The discriminating power of a combined ultrasonic/neutron activation analysis sensor system is shown in FIG. 2. In this figure, the x-axis corresponds to the density of the material (output of ultrasonic detector) and the y axis corresponds to the atomic ratio (wt %) element in the compound (output of neutron activation analysis detector). Although the densities of hazardous liquids, such as nitromethane and nitroglycerin, are significantly different from non-hazardous liquids such as water, discrimination that solely bases on density is likely to cause a significant number of false alarms because of variations in the measurement (width of bottle, temperature of liquid, etc). The combination of ultrasonics and neutron activation analysis provides a much more reliable method of detection.

Accordingly, a container may be screened using a combination of two or three detection technologies that compensate with each other. Detection by different sensors may be conducted sequentially or simultaneously.

The processing unit 130 receives data from the sensor and the UPC reader. The microprocessor 132 compares the data to corresponding finger prints of various hazardous and non-hazardous materials stored in the memory 134, and makes a determination of the materials contained inside the container using an algorithm stored in the memory 134. Algorithms for chemical detection and identification and quantification are well known in the art and are also commercially available. A library of sensor signatures for various hazardous and non-hazardous materials is stored in the memory 134. As used herein, a sensor signature is a sensor measurement that is characteristic to a particular substance and can be used to identify that substance. A library of UPC barcodes is also stored in the memory 134. In one embodiment, the memory 134 can be a flash memory or a DRAM.

The display device 140 displays the detection result from the sensors. In one embodiment, a final result (after combining data from all detectors) is shown on the display device 140 as either "pass" or "fail," so that non-technical personnel may operate the container screening system. In another embodiment, an alarm sign is displayed on the display device 140 when an ultra-hazardous material, such as a liquid explosive or a precursor of a liquid explosive, is identified in the container so that the operator may detain the owner of the container.

Figure 3:
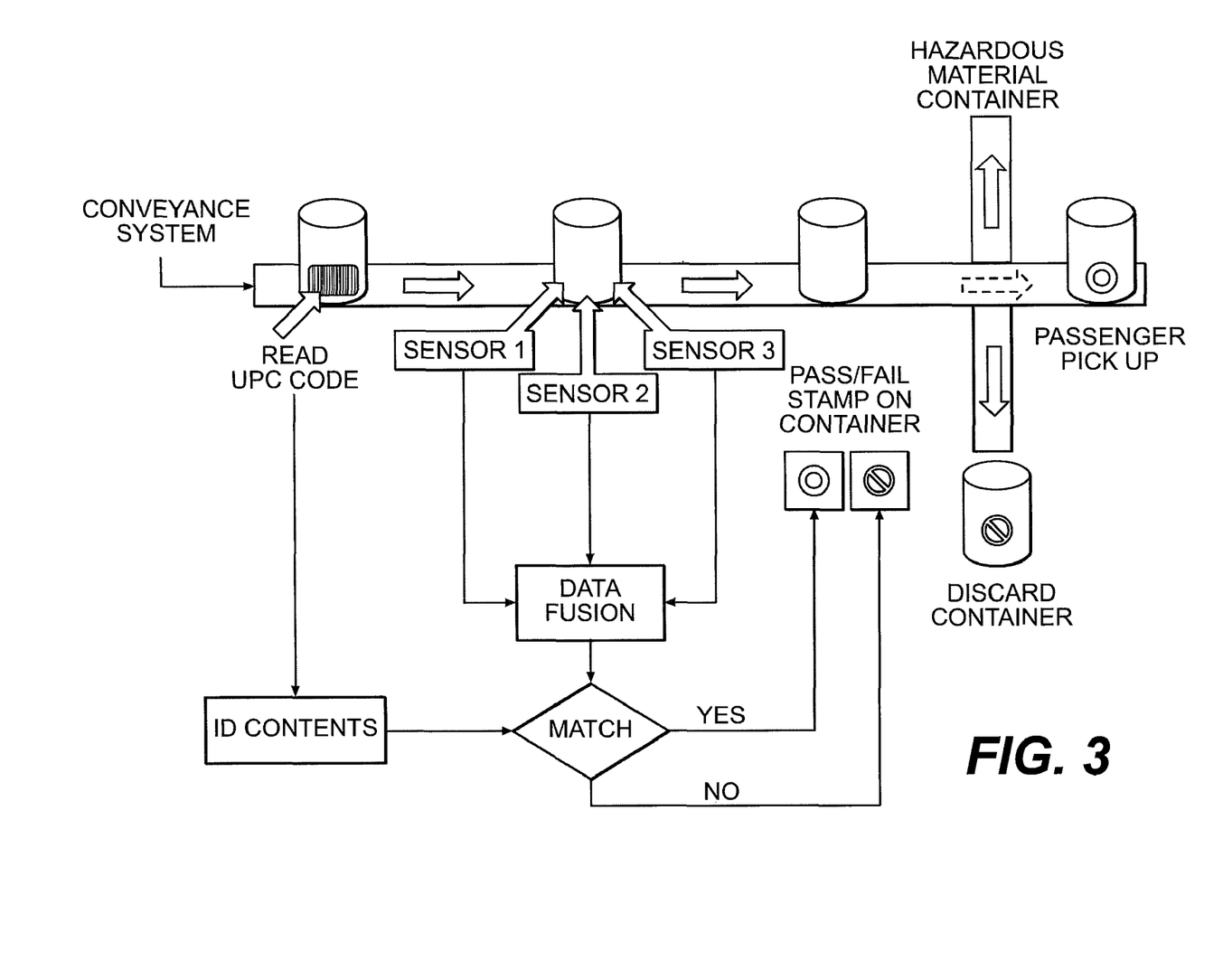
FIG. 3 is a diagram showing the workflow of an embodiment of the container screening system of the present invention.

FIG. 3 shows an exemplary workflow of the container screening system of the present invention at an airport check point. As containers moving into the system on the conveyance belt, the UPC reader will scan all containers for a UPC. For containers having a UPC, the system will determine what the contents of the containers should be based on the UPC, i.e., a Coca-Cola bottle should contain Coca-Cola. The content information will be fed into an algorithm which will read data from other sensors in the system, compare the sensor data to a library of sensor signatures, and identify the contents of the container based on the sensor data from one or more sensors in the system.

If the sensor data match the UPC signature (i.e., the Coca-Cola bottle does contain Coca-Cola), the container will be marked with a fluorescent, easily seen marking. Only containers of liquid with the fluorescent marking will be allowed on board an aircraft. If the sensor data does not match the UPC signature, or if the container does not have a UPC, the system will search the sensor signature library for the closest match to the sensor data. If the container is identified as having a hazardous material, the container will be moved to a safe storage container off the main path of the conveyor and local TSA personnel warned of a possible hazardous container. If the system cannot identify the material in the container, then the container will be discarded into a trash container. All containers with unidentified material inside or with possible explosive materials will be marked with a clearly visible fluorescent marker, different from the marker used to mark safe bottles. In one embodiment, containers with unidentified materials are marked differently from containers with identified hazardous materials. Containers with identified ultra-hazardous materials, such as liquid explosives or precursors of liquid explosives, may be marked with yet another fluorescent marker and moved to an explosion-proof container.

Figure 4:
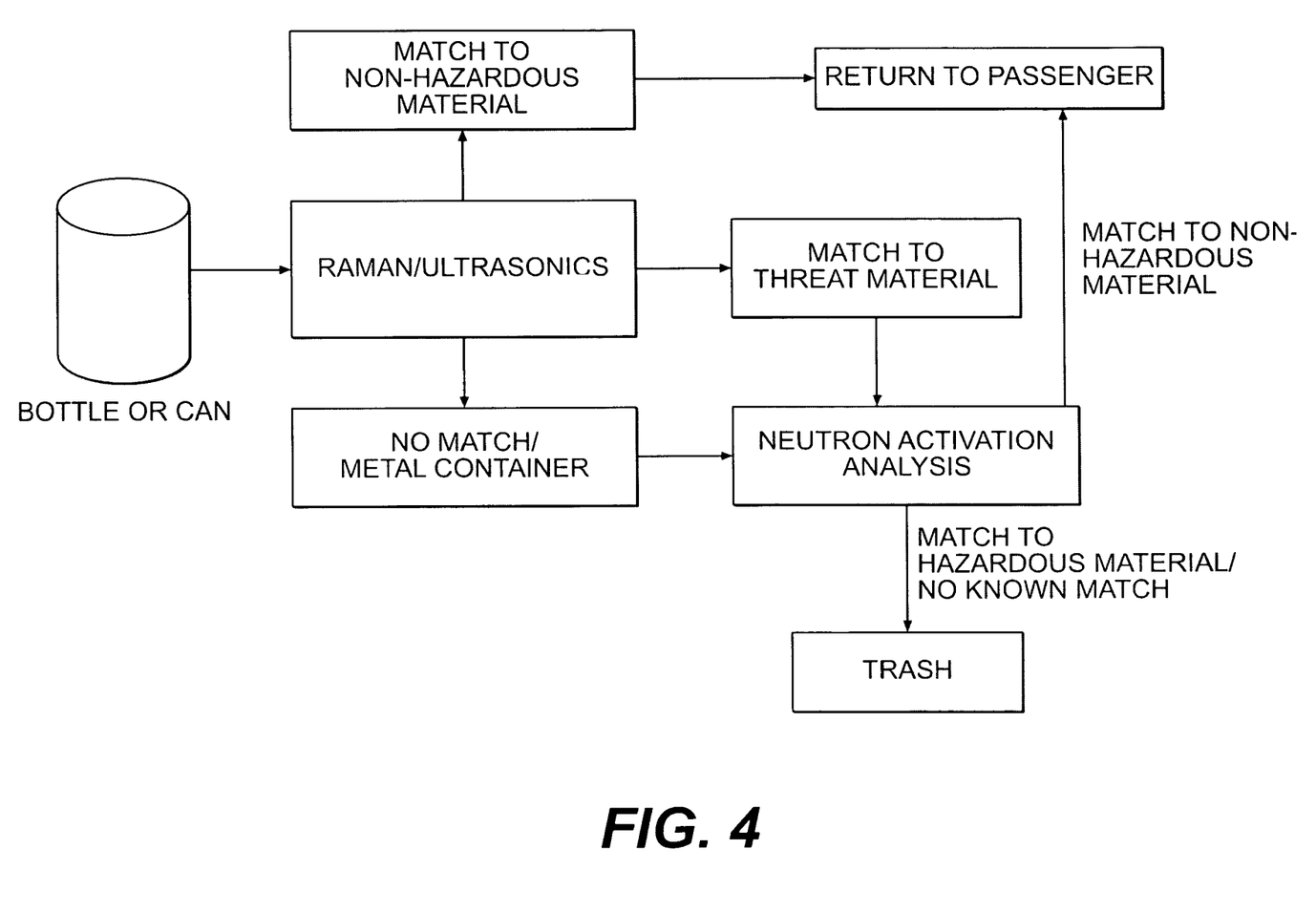
FIG. 4 is a diagram showing the operation of a Raman/ultrasonic trigger combined with a neutron activation analysis.

FIG. 4 shows another embodiment of the container screen system of the present invention. The system uses the less expensive ultrasonic and Raman sensors as a prescreening system. Containers are first screened by ultrasonics and Raman sensors.

If the contents of the containers are positively identified as non-hazardous materials by the ultrasonics and Raman sensors, the containers will be returned to passenger without further inspection.

If the ultrasonics and Raman sensors indicate a hazardous material in the containers, the bottle will be moved to the trash container or subject to further analysis by the neutron activation analysis detector.

If the ultrasonics and Raman sensors cannot make a definitive identification, or if the containers is opaque or metal (Raman technology will not work on opaque or metal containers), the containers are then scanned using the more expensive neutron activation analysis detector. Containers with contents that are positively identified as non-hazardous materials by the neutron activation analysis detector will be returned to passenger. Containers with contents that are still unidentifiable or contents that are identified as hazardous materials by the neutron activation analysis detector will be moved to a trash container.

The advantage to using the ultrasonics and Raman spectroscopy as a prescreening system is that the more expensive neutron activation analysis can be multiplexed to a number of less expensive ultrasonics/Raman prescreening systems. The prescreening system will fuse the ultrasonic and Raman detector's results and determine if the container contains hazardous materials. In a case where the prescreening system cannot make a high probability match, then the container or containers are sent to a neutron activation analysis detector for further inspection. The identity of the materials inside the container will be determined by fusing the data from all three detectors. This approach allows for the multiplexing of the more expensive neutron activation analysis technology, saves on the initial cost and will increase throughput of the system. In one embodiment, the detection system of the present invention is capable of screening 200 containers per hour and small enough to be fitted into existing airport passenger checkpoint areas.

Figure 5:
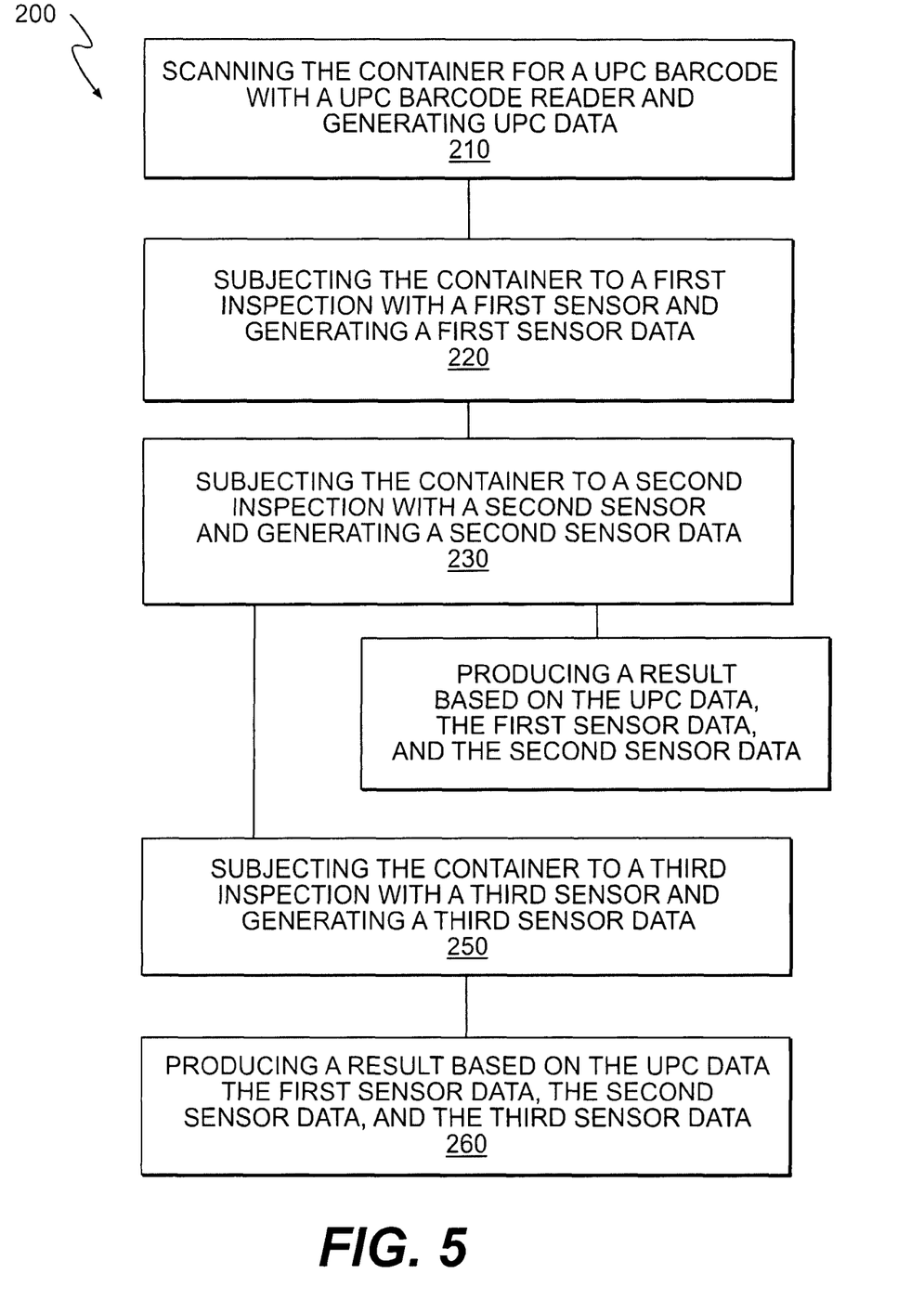
FIG. 5 is a flow chart showing an embodiment of the screening method of the present invention.

Another aspect of the present invention relates to a method 200 of screening a container for hazardous materials (FIG. 5). The method 200 comprises the steps of scanning (210) the container for a UPC and generating UPC data, subjecting (220) the container to a first inspection with a first sensor and generating first sensor data, subjecting (230) the container to a second inspection with a second sensor and generating second sensor data, and producing (240) a screening result based the UPC data, the first sensor data and the second sensor data, wherein the first sensor and the second sensor use different technologies for the detection of the hazardous materials.

In another embodiment, the method 200 further comprises the step of subjecting (250) the container to a third inspection with a third sensor and generating third sensor data. The result is produced based on the UPC data, the first sensor data, the second sensor data, and the third sensor data (step 260).

In another embodiment, the first sensor uses ultrasonic spectroscopy technology and the second sensor uses Raman detection technology.

In another embodiment, the third sensor uses neutron activation analysis technology.

In yet another embodiment, the method 200 comprises the steps of scanning (210) the container for UPC with a UPC reader and generate UPC data; subjecting (220) the container to a first inspection with ultrasound technology and generate ultrasonic data; subjecting (230) the container to a second inspection with Raman spectroscopy technology and generating Raman data; determining (240) identities of materials inside the container based on the UPC data; the ultrasonics data and the Raman data; if all materials inside the container are identified as non-hazardous materials, allowing the container to pass inspection; if one or more materials inside the container is identified as hazardous material, transporting the container to a storage device; if one or more materials inside the container are unidentified, subjecting (250) the container to inspection with neutron activation technology, and determining (260) identities of materials inside the container based on the UPC data, the ultrasonic data, the Raman data, and the neutron activation analysis data.

EXAMPLES

Example 1

Figure 6A:
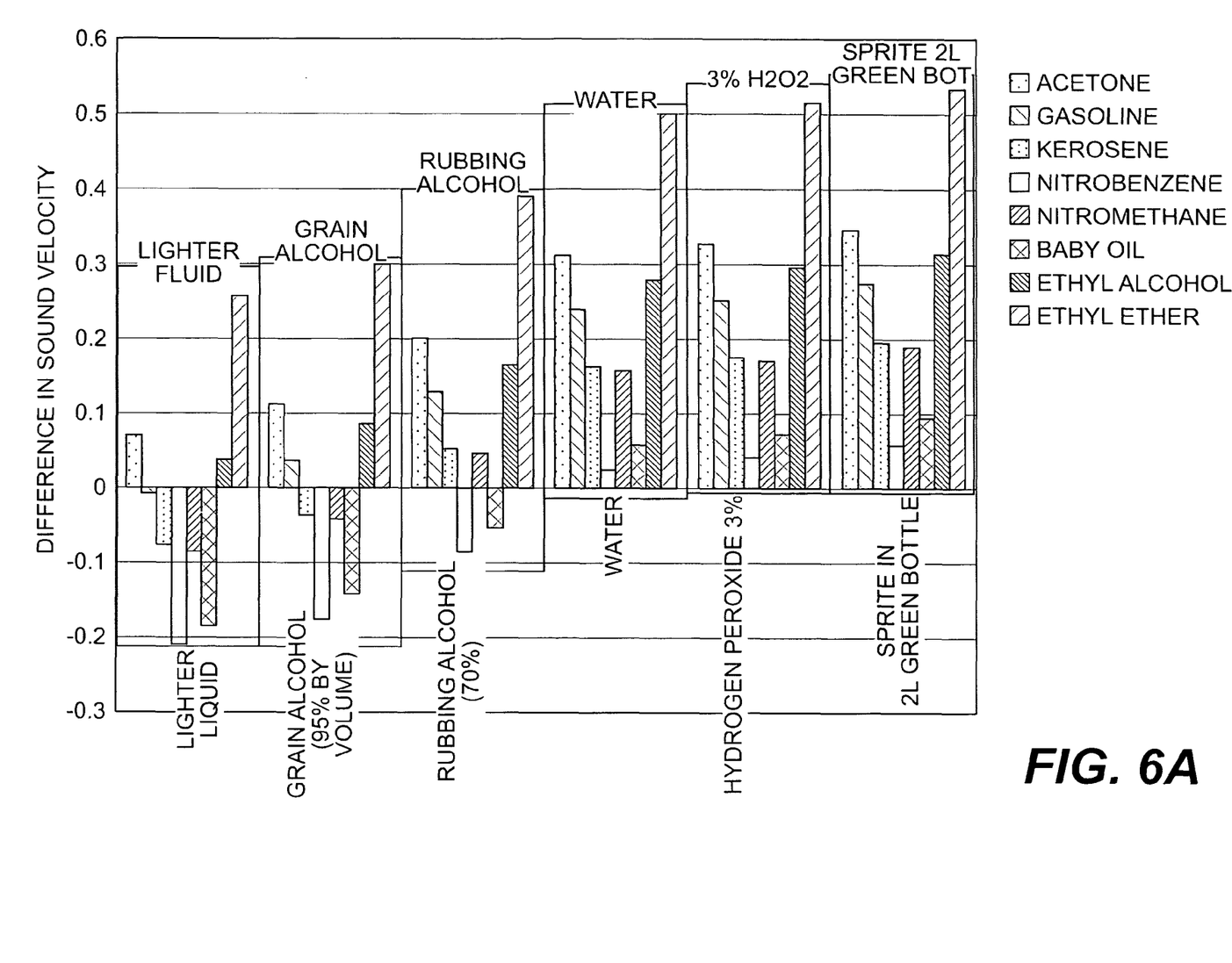
FIGS. 6A and 6B are diagrams showing differences between the sound velocity in a target material and all the other hazardous materials shown in the legend. The target material is marked on top of each box. For example, the fourth box from the left in FIG. 6A shows the difference in sound velocity between water and the hazardous materials shown in the legend on the right.
Figure 6B:
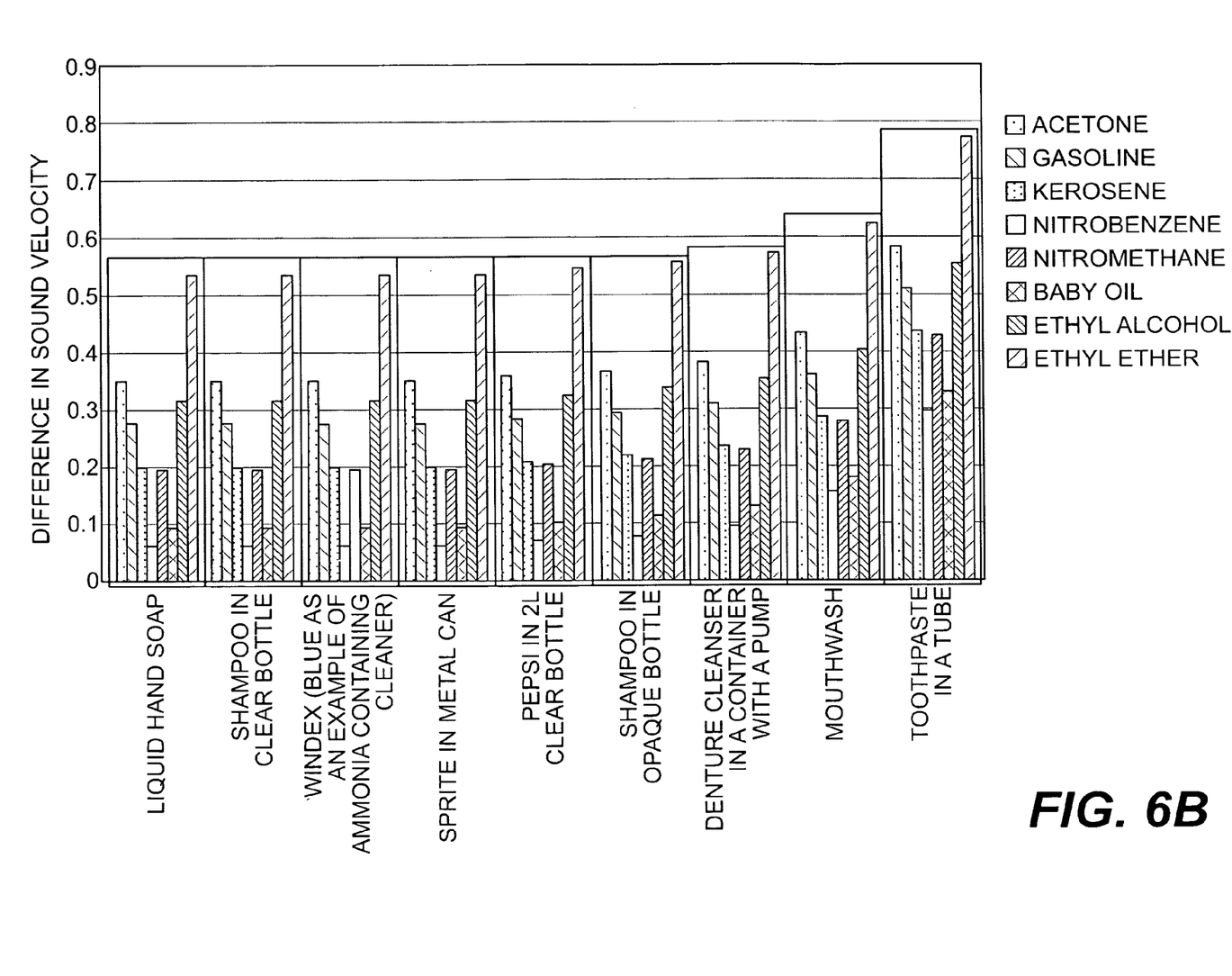

Discrimination of Hazardous Materials from Non-Hazardous Materials by Ultrosonic Technique A number of hazardous and non-hazardous materials were screened with a HILDA Hazardous Liquid Detection Apparatus that uses an ultrasonic detection method (Spearhead Innovations, Inc., Arlington, Va.). The container is placed into HILDA's sample chamber and the ultrasonic transducers contacted with the container. In HILDA, the ultrasonic microphone is fixed and the ultrasonic transducer is on a spring loaded arm. The spring loaded arm is pulled such that the container will fit into the gap between the ultrasonic transducer and microphone. Then the arm is allowed to close onto the container contacting the ultrasonic transducer and microphone onto the container walls. As shown in FIGS. 6A and 6B, the ultrasonics are able to discriminate between the hazardous liquid materials (nitromethane, lighter fluid, gasoline, acetone) and the regular liquids people may carry (water, sprite, hand soap, shampoo, etc) based on the difference in sound velocity in these materials.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A container screening system for detecting hazardous materials in a container, comprising:
    a universal product code (UPC) reader that reads a UPC barcode from said container;
    a first sensor that detects materials inside said container using a first detection technology;
    a second sensor that detects materials inside said container using a second detection technology, wherein said second detection technology is different from said first detection technology; and
    a data processing unit that processes data from said first sensor and said second sensor, and identifies a material inside said container based on the UPC barcode and data from said first sensor and said second sensor,
    wherein said UPC reader is used as a queuing device for the first and second sensor, and wherein said first detection technology is ultrasonics and said second detection technology is Raman spectroscopy.

2. The container screening system of claim 1, further comprises a third sensor that detects materials inside said container using a third detection technology, wherein said third detection technology is different from said first detection technology and said second detection technology.

3. The container screening system of claim 2, wherein said first, second, and third sensors can be used sequentially or simultaneously.

4. The container screening system of claim 1, further comprising a conveyor system that transports said container.

5. The container screening system of claim 1, further comprising a display device that displays a screening result.

6. The container screening system of claim 1, further comprising a marking device that places a mark on said container after screening.

7. The container screening system of claim 1, wherein said data processing unit comprises a microprocessor and a memory, wherein said memory is used to store sensor signatures of hazardous and non-hazardous materials.

8. The container screening system of claim 1, wherein said hazardous materials comprises liquid explosives and precursors of liquid explosives.

9. A container screening system for detecting hazardous materials in a container, comprising:
    a universal product code (UPC) reader that reads a UPC barcode from said container;
    a first sensor that detects materials inside said container using a first detection technology;
    a second sensor that detects materials inside said container using a second detection technology, wherein said second detection technology is different from said first detection technology;
    a third sensor that detects materials inside said container using a third detection technology, wherein said third detection technology is different from said first detection technology and said second detection technology, and
    a data processing unit that processes data from said first sensor and said second sensor, and identifies a material inside said container based on the UPC barcode and data from said first sensor and said second sensor,
    wherein said UPC reader is used as a queuing device for the first and second sensor and wherein said third detection technology is neutron activation analysis.

10. A method of screening a container for hazardous materials, comprising:
    scanning said container with a UPC reader and generating UPC data;
    subjecting the container to a first inspection with a first sensor using a first detection technology and generating first sensor data;
    subjecting the container to a second inspection with a second sensor using a second detection technology and generating second sensor data, and
    producing a screening result based on said UPC data, said first sensor data and said second sensor data,
    wherein said UPC data is used to queue said first inspection and said second inspection and wherein said first detection technology is different from said second detection technology and wherein said first detection technology is ultrasonics and said second detection technology is Raman spectroscopy.

11. The method of claim 10, further comprising:
    subjecting said container to a third inspection with a third sensor using a third detection technology and generating a third sensor data,
    wherein said third detection technology is different from said first detection technology and said second detection technology, and wherein said screening result is produced based on said UPC data, said first sensor data, said second sensor data, and said third sensor data.

12. The method of claim 11, wherein said third detection technology is neutron activation analysis.

13. The method of claim 10, further comprising:
marking said container based on said screening result.

14. The method of claim 10, further comprising displaying said screen result on a display device.

15. The method of claim 10, wherein said hazardous materials comprise liquid explosives and precursors of liquid explosives.

16. The method of claim 15, further comprising:
storing containers that are screened positive for liquid explosives or precursors of liquid explosives in a explosion-proof container.

17. A method of screening a container for hazardous materials, comprising:
scanning said container for UPC barcode with a UPC reader and generating UPC data as a queuing device;
subjecting said container to a first inspection with a first sensor using a first detection technology and generating first sensor data;
subjecting said container to a second inspection with a second sensor using a second detection technology and generating second sensor data;
identifying materials inside said container based on said UPC data said first sensor data and said second sensor data;
if all materials inside said container are identified as non-hazardous materials, allowing said container to pass inspection;
if one or more materials inside said container is identified as hazardous material, transporting the container to a storage device;
if one or more materials inside the container cannot be identified by the first detection technology and the second detection technology, subjecting said container to inspection with a third sensor using a third detection technology and generating a third sensor data, and
identifying said one of more materials that cannot be identified by the first detection technology and the second detection technology based on said third sensor data.

18. The method of claim 17, wherein said first detection technology is ultrasonics, said second detection technology is Raman spectroscopy, and said third detection technology is neutron activation analysis.

* * * * *